US007015339B2

(12) United States Patent
Khare et al.

(10) Patent No.: US 7,015,339 B2
(45) Date of Patent: Mar. 21, 2006

(54) PROCESS FOR ISOLATING PHENOLIC COMPOUNDS

(75) Inventors: Anil Bhagwan Khare, Crystal, MN (US); Brent Howard Hilbert, South Haven, MN (US)

(73) Assignee: Cargill, Incorporated, Wayzata, MN (US)

( * ) Notice: Subject to any disclaimer, the term of this patent is extended or adjusted under 35 U.S.C. 154(b) by 272 days.

(21) Appl. No.: 10/201,191

(22) Filed: Jul. 23, 2002

(65) Prior Publication Data

US 2003/0139610 A1 Jul. 24, 2003

Related U.S. Application Data

(60) Provisional application No. 60/307,530, filed on Jul. 24, 2001.

(51) Int. Cl.
*C07D 319/14* (2006.01)
(52) U.S. Cl. .......................... 549/362; 536/8; 536/128
(58) Field of Classification Search ................ 549/362; 514/456; 536/128, 8
See application file for complete search history.

(56) References Cited

U.S. PATENT DOCUMENTS

| | | | |
|---|---|---|---|
| 2,952,674 A * | 9/1960 | Merritt et al. ................ | 536/8 |
| 3,461,205 A | 8/1969 | Mansfeld et al. | |
| 4,157,984 A | 6/1979 | Zilliken | |
| 4,218,489 A | 8/1980 | Zilliken | |
| 4,232,122 A | 11/1980 | Zilliken | |
| 4,264,509 A | 4/1981 | Zilliken | |
| 4,366,082 A | 12/1982 | Zilliken | |
| 4,366,248 A | 12/1982 | Zilliken | |
| 4,390,559 A | 6/1983 | Zilliken | |
| 4,428,876 A | 1/1984 | Iwamura | |
| 5,141,746 A | 8/1992 | Fleury et al. | |
| 5,244,887 A | 9/1993 | Straub | |
| 5,670,632 A | 9/1997 | Chaihorsky | |
| 5,679,806 A | 10/1997 | Zheng et al. | |
| 5,702,752 A | 12/1997 | Gugger et al. | |
| 5,792,503 A | 8/1998 | Gugger et al. | |
| 5,821,361 A * | 10/1998 | Waggle et al. .............. | 536/128 |
| 5,919,921 A | 7/1999 | Waggle et al. | |
| 5,936,069 A | 8/1999 | Johnson | |
| 5,968,516 A | 10/1999 | Liu | |
| 5,990,291 A | 11/1999 | Waggle et al. | |
| 6,013,771 A | 1/2000 | Shen et al. | |
| 6,033,714 A | 3/2000 | Gugger et al. | |
| 6,040,333 A | 3/2000 | Jackson | |
| 6,171,638 B1 | 1/2001 | Gugger et al. | |
| 6,261,565 B1 | 7/2001 | Empie et al. | |
| 6,323,018 B1 | 11/2001 | Waggle et al. | |
| 6,355,816 B1 | 3/2002 | Dobbins | |
| 6,495,141 B1 | 12/2002 | Waggle et al. | |

FOREIGN PATENT DOCUMENTS

| | | |
|---|---|---|
| EP | 0 426 998 | 5/1991 |
| EP | 0 647 408 A1 | 4/1995 |
| EP | 0 947 197 A1 | 10/1999 |
| EP | 1 038 531 A2 | 9/2000 |
| EP | 0 795 553 B1 | 1/2002 |
| JP | 62126186 A | 6/1987 |
| JP | 4036242 A | 2/1992 |
| JP | 4266898 A | 9/1992 |
| JP | 6287554 A | 10/1994 |
| JP | 10316671 | 12/1998 |
| WO | WO 95/10530 | 4/1995 |
| WO | WO 96/30468 | 10/1996 |
| WO | WO 00/03684 | 1/2000 |
| WO | WO 01/43566 | 6/2001 |
| WO | WO 01/43566 A1 | 6/2001 |
| WO | WO 01/51482 | 7/2001 |
| WO | WO 01/51482 A1 | 7/2001 |

OTHER PUBLICATIONS

Barnes et al., "Isoflavones and Their Conjugates in Soy Foods: Extraction Conditions and Analysis by HPLC—Mass Spectrometry," *J. Agric. Food Chem.*, 1994, 42:2466-2474.

Nguyenle et al., "An investigation on the extraction and concentration of isoflavones in soy-based products," *J. Pharm. Biome. Anal.*, 1995, 14:221-232.

Jones et al., "Development and Application of a High-performance Liquid Chromatographic Method for the Analysis of Phytoestrogens," *J. Sci. Food Agric.*, 1989, 46:357-364.

* cited by examiner

*Primary Examiner*—Taofiq Solola
*Assistant Examiner*—Robert Shiao

(57) ABSTRACT

The invention provides compositions and methods for isolating phenolic compounds, particularly isoflavones, from aqueous extracts of plant materials that contain such compounds. The process comprising:
  (a) providing an aqueous plant extract at a first pH less than 10, the aqueous plant extract comprising a plurality of phenolic compounds;
  (b) extracting the aqueous plant extract with a first organic solvent to yield a first organic extract;
  (c) extracting the first organic extract with an aqueous phase of pH greater than 10 to yield a phenol rich aqueous phase;
  (d) adjusting the pH of the phenol rich aqueous phase to a pH of less than 9; and
  (e) isolating the phenolic compounds from the phenol rich aqueous phase.

29 Claims, No Drawings

PROCESS FOR ISOLATING PHENOLIC COMPOUNDS

RELATED APPLICATION

This Application claims priority from and benefit of U.S. provisional application No. 60/307,530.

TECHNICAL FIELD

This invention relates to methods for isolating phenolic compounds from plant materials, and more particularly to methods for isolating isoflavones from plant materials such as soybean extracts.

BACKGROUND

Plants are a natural warehouse of bioactive compounds. The primary difficulty in accessing this abundant diversity of compounds lies in the problematic separation of the various components. Isoflavones are an example of an interesting class of phenolic containing plant flavonoid compounds which are believed to have a number of beneficial health effects on mammals. For example, isoflavones have been suggested to provide a beneficial effect on the symptoms experienced by menopausal and peri-menopausal women. Currently 15% of menopausal women are on Hormone Replacement Therapies (HRT) that employ animal estrogens. HRT products derived from animal estrogens are highly potent and activate all estrogen receptors. This potency is correlated with an increased risk of breast cancer and other complications. Since plant isoflavones have a lower affinity to the estrogen receptor, they may be preferred to animal estrogens for some uses. In addition, some research has indicated isoflavones may even prevent or retard certain cancers, such as breast and prostate cancers, as well as have serum cholesterol-lowering effects.

Despite the beneficial effects associated with plant isoflavones, many individuals have not increased their intake of isoflavones, particularly those available from soy foods, because the variety of soy based foods in many countries have been limited and because many find the flavor and colors of soy foods bitter and unappetizing. Thus, it would be desirable to provide methods for isolating isoflavones from a variety of plant materials with improved purity, color, flavor, solubility, and shelf stability to promote the incorporation of these beneficial nutrients in a variety of food, beverage, dietary supplement, and pharmaceutical products.

SUMMARY OF THE INVENTION

The present invention provides a method for isolating phenolic compounds comprising the steps of:
  (a) providing an aqueous plant extract at a first pH greater than 10, the aqueous plant extract comprising a plurality of phenolic compounds;
  (b) washing the aqueous plant extract with an organic solvent;
  (c) adjusting the pH of the aqueous plant extract to a pH of less than 9; and
  (d) isolating the phenolic compounds from the aqueous plant extract.

The present invention also provides a method for isolating phenolic compounds comprising:
  (a) providing an aqueous plant extract at a first pH less than 10, the aqueous plant extract comprising a plurality of phenolic compounds;
  (b) extracting the aqueous plant extract with a first organic solvent to yield a first organic extract;
  (c) extracting the first organic extract with an aqueous phase of pH greater than 10 to yield a phenol rich aqueous phase;
  (d) adjusting the pH of the phenol rich aqueous phase to a pH of less than 9; and
  (e) isolating the phenolic compounds from the phenol rich aqueous phase.

The present invention also provide a composition comprising:
  a) two or more isoflavones wherein the isoflavones represent greater than 15 percent by weight of the composition, and
  b) the composition exhibits about 80% or greater solubility in a mixture comprising about 0.03% by weight of the composition in water.

The present invention also provides a isoflavone composition wherein upon combustion of the composition an ash content of less than about 25% is determined.

The present invention also provides a isoflavone composition wherein the composition has an L-color value of greater than about 65.

The present invention also provides a isoflavone composition wherein the composition comprises daidzin and genistin and the ratio of the weight percent of daidzin to the weight percent of genistin is greater than one, and wherein the diadzin and genistin are present in either the aglycone or glycoslyated form.

The present invention also provides a isoflavone composition wherein;
  a) the composition exhibits greater than about 90% solubility,
  b) upon combustion the ash content is less than about 10%,
  c) the composition has an L-color value of greater than about 75 and an a-color value of less than 2,
  d) the composition comprises daidzin, glycitin, and genistin and the ratio of the weight percent of daidzin to the weight percent of genistin is greater than two and the ratio of the weight percent of glycitin to the weight percent of genistin is greater than two, and
  e) greater than 95% the isoflavones are in the form of free glycosides.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the detailed description below. Other features, objects, and advantages of the invention will be apparent from the detailed description and from the claims.

DETAILED DESCRIPTION

The invention provides methods for isolating phenolic compounds, particularly isoflavones, from aqueous extracts of plant materials that contain such compounds. The invention also provides compositions of isoflavones. The methods utilize temperature, solvent, and pH regimes to separate the phenolic compounds from the major contaminants found in crude aqueous plant extracts containing isoflavones. Selective partitioning, extracting, purifying, isolating, and converting of the desired isoflavones promotes increased recovery, stability, and purity of the desired isoflavones. The resulting isoflavone compositions have enhanced color, flavor, odor, solubility, and shelf-life characteristics.

The present invention employs a process of adjusting the pH of solutions and mixtures. Any known base may be used to raise the pH of an aqueous solution or mixture, including sodium hydroxide, potassium hydroxide, calcium hydroxide, cesium hydroxide, lithium hydroxide, or ammonia. Any of the many known organic or inorganic acids may be used to lower the pH of aqueous solutions or mixtures including acetic, hydrochloric, sulfuric, phosphoric, nitric, oxalic, sulfurous, or chlorous acids.

Phenolic containing, particularly isoflavone containing, aqueous plant extracts may be prepared from any plant material containing such compounds by methods well known and described in the art. Plant materials containing phenolic or polyphenolic compound include but are not limited to fruits, vegetables, grains, nuts, tea, wine, grasses, and the like. Any plant material which contains phenolic compounds, stable at pH >10, may be used in the process of the present invention. Plant materials containing isoflavones include plants and plant by-products of soybean, chick pea, red clover, subterranean clover, ground pea, milk vetch, marama bean, sword bean, jack bean, seaside sword bean, carao bean, cluster bean, balu, hyacinth bean, grass pea, Indian vetch, garden pea, djenko bean, goa bean, yam bean, broad bean, earth pea, lentil, jumping bean, alfalfa, velvet bean, African locust bean, inga, Cyprus vetch, yebnut, tallow tree, Polynesian chestnut, kudzu root, oil bean tree, mesquite, tamarind, fenugreek, Indian licorice, and ground nut and preparations of such plant materials such as defatted soy flakes, soy flour, soy germ flour, and soy meal.

The term "Phenolic Compounds" as used herein include compounds containing a phenolic subunit. The subunit maybe linked, bound, or fused to any other type of molecular structure. Preferred phenolic compounds included those from plant extracts (plant phenolic compounds). Other preferred phenolic compounds include compounds containing more than one hydroxy substituant on the phenolic subunit or compounds with more than one phenolic subunits (polyphenolic compounds). Especially preferred polyphenolic compounds are those from plant extracts (plant polyphenolic compounds). Polyphenolic compounds include but are not limited to phenolic acids and flavonoids.

The term "Flavonoids" as used herein would be readily understood by one skilled in the art (see e.g. H. Merken and G. Beecher, *J. of Agricultural and Food Chemistry*, Vol 48, No. 3, 2000) and includes but is not limited to anthocyanidins, flavones/flavonols, flavanones, and proanthocyanidins.

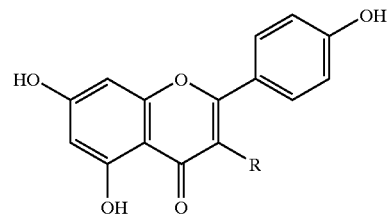

Flavonoid General Structure
(R = H in flavones and R = OH in flavonols)

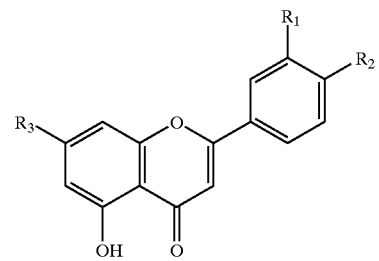

Flavanone General Structure

| Flavanone | R1 | R2 | R3 |
|---|---|---|---|
| Didymin | H | OMe | ORut |
| Eriocitrin | OH | OH | ORut |
| Eriodietyol | OH | OH | OH |
| Hesperetin | OH | OMe | OH |
| Hesperidin | OH | OMe | ORut |
| Isoakuranetin | H | OMe | OH |
| Naringenin | H | OH | OH |
| Naringin | H | OH | ONeo |
| Narirutin | H | OH | ORut |
| Neoeriocitrin | OH | OH | ONeo |
| Noehesperidin | OH | OMe | ONeo |
| Pinocembrin | H | H | OH |
| Poncirin | H | OMe | ONeo |

Rut = rutinoside
Neo = neosesperidose

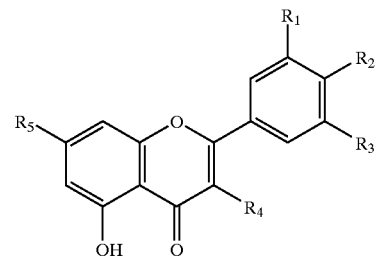

Flavonol General Structure

| Flavonol | R1 | R2 | R3 | R4 | R5 |
|---|---|---|---|---|---|
| Astragalin | H | OH | H | OGlu | OH |
| Hyperoside | OH | OH | H | OGal | OH |
| Isoquercitrin | OH | OH | H | OGlu | OH |
| Isorhammetin | OMe | OH | H | OH | OH |
| Kaempferide | H | OMe | H | OH | OH |
| Kaempferol | H | OH | H | OH | OH |

Flavonol General Structure

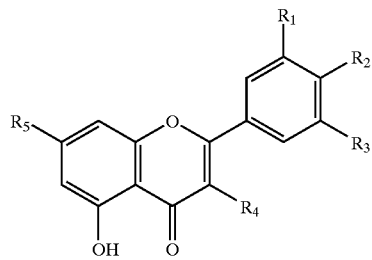

| Flavonol | R1 | R2 | R3 | R4 | R5 |
|---|---|---|---|---|---|
| Myricetin | OH | OH | OH | OH | OH |
| Quercetin | OH | OH | H | OH | OH |
| Quercitrin | OH | OH | H | ORham | OH |
| Rhamnetin | OH | OH | H | OH | OMe |
| Rutin | OH | OH | H | ORut | OH |

Rut = rutinose
Gla = glactose
Glu = glucose
Rham = rhamnose

Flavone General Structure

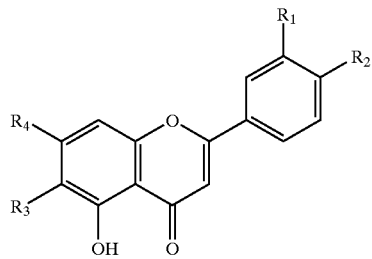

| Flavone | R1 | R2 | R3 | R4 |
|---|---|---|---|---|
| Apigenin | OH | H | H | OH |
| Baicalein | H | H | OH | OH |
| Chrysin | H | H | H | OH |
| Diosmin | OMe | OH | H | ORut |
| Genkwanin | OH | H | H | OMe |
| Isorhoifolin | OH | H | H | ORut |
| Lureolin | OH | OH | H | OH |
| Rhoifolin | OH | H | H | ONeo |
| Techtochrysin | H | H | H | OMe |

Rut = rutinose
Gla = glactose
Glu = glucose
Rham = rhamnose

Anthocyanidin General Structure

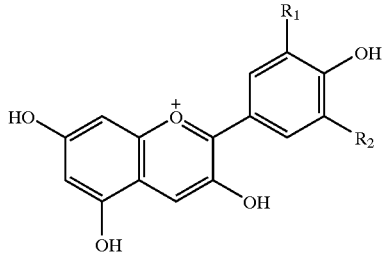

| Anthocyandin | R1 | R2 |
|---|---|---|
| Cyanidin | H | OH |
| Delphinidin | OH | OH |
| Malvindin | OMe | OMe |
| Pelargonidin | H | H |
| Pelunidin | OMe | OH |
| Peonidin | OMe | H |

TABLE 1

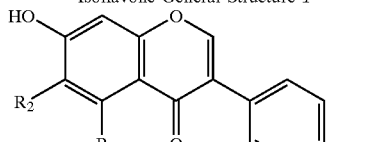

Aglycone Isoflavone General Structure.

| Isoflavone | Formula | MW | R₁ | R₂ |
|---|---|---|---|---|
| Daidzein | $C_{15}H_{10}O_4$ | 254.24 | H | H |
| Genistein | $C_{15}H_{10}O_5$ | 270.24 | OH | H |
| Glycitein | $C_{16}H_{12}O_5$ | 284.26 | H | $OCH_3$ |

Glycosylated isoflavones found in soy can have the general structure below (structure 2) as further described in the table.

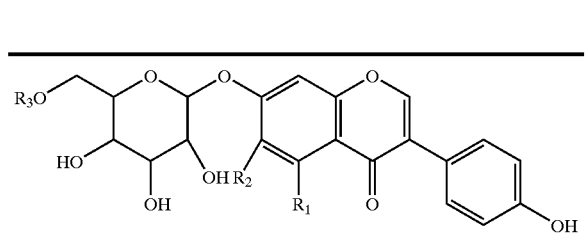

Glycosylated Isoflavone General Structures.

| Isoflavone | R₁ | R₂ | R₃ |
|---|---|---|---|
| Daidzin | H | H | H |
| Genistin | OH | H | H |
| Glycitin | H | $OCH_3$ | H |
| Acetyldaidzen | H | H | $COCH_3$ |
| Acetylgenistin | OH | H | $COCH_3$ |
| Acetylglycitin | H | $OCH_3$ | $COCH_3$ |
| Malonyldaidzin | H | H | $COCH_2COOH$ |
| Malonylgenistin | OH | H | $COCH_2COOH$ |
| Malonylglycitin | H | $OCH_3$ | $COCH_2COOH$ |

In particular, isoflavone containing aqueous plant extracts can be prepared from soybean or clover, which are known to contain elevated concentrations of isoflavones. For example, aqueous plant extracts can be prepared from soybeans, soy meal, soy flakes, soy flour, soy germ, soy germ flour, soy molasses (also known as soy solubles), Novasoy®, soy whey, or any other concentrated isoflavone product. Soy germ fractions are particularly useful as a starting material because they contain elevated levels (approximately 2% on a weight per weight basis) of isoflavones compared to other soybean fractions. Methods are known for preparing soy meal, soy flakes, soy flour, soy germ, soy germ flour, soy molasses (also known as soy solubles), Novasoy®, and soy whey from soybeans. (see e.g. Erickson D. R., *Practical Handbook of Soybean Processing and Utilization*, AOCS Press, 1995 and U.S. Pat. No. 5,702,752 describing methods for preparing soy molasses.) Soy whey is a liquid formed from the isoelectric or divalent cation precipitation of the solubilized fraction that results from the processing of soybeans into soy foods as described in U.S. Pat. No. 6,033,714. Novasoy® has been described as a soy derived product and is available from the Archer Daniels Midland Company.

When soybeans or soy germ are employed as starting materials, they can be pre-treated with conventional well known methods of oil extraction. (see e.g. Wan Peter J., *Technology and Solvents for Extracting Oilseeds and Non-petroleum Oils*, AOCS Press, 1997.) For examples, cracking raw soy beans, dehulling, flaking, and extraction with an organic solvent such as hexane. After desolventizing, the resulting soy bean meal or white flakes from the oil extraction maybe then extracted with an aqueous alcohol, such as ethanol at 60–80° C. After extracting, the alcohol is preferentially, but need not be, removed resulting in a crude aqueous plant extract having an approximately neutral pH of about 6–8. Accordingly, aqueous plant extracts useful in the present invention will often have residual amounts of various other solvents. See, for example, U.S. Pat. No. 6,132,795, which exemplifies other conventional methods for preparing crude aqueous plant extracts containing isoflavones from plant materials.

not limited to ultrafiltration and adsorption chromatography. Additionally, pre-purification may further include spray drying and re-crystallization of plant extracts. See, for example, U.S. Pat. Nos. 5,702,752; 5,792,503; 6,033,714; and 6,171,638. The resulting phenolic or isoflavone containing fractions may be appropriately treated and/or resuspended in an aqueous solution before processing according to the present invention.

Soybeans and soy foods are common dietary sources of isoflavones. Isoflavones present in soy include both isoflavone aglycones and isoflavone glycosides, wherein a glucose molecule is attached via a glycosidic bond to the isoflavone backbone. Isoflavone aglycones present in soy include but are not limited to daidzein, genistein, and glycitein. The isoflavone glycoside compounds present in soy include: daidzin, genistin, glycitin, 6"-O-acetyldaidzin, 6"-O-acetylgenistin, 6"-O-acetylglycitin, 6"-O-malonyldaidzin, 6"-O-malonylgenistin, and 6"-O-malonylglycitin. The 6"-O acetyl and the 6"-O malonyl isoflavones are esterified derivatives of the glucose molecule at the 6 position. Approximately, ninety-seven to ninety-eight percent of the naturally occurring isoflavones in soybeans are in the glycosylated form.

The major contaminants in crude aqueous alcohol extracts containing isoflavones are saponins, oligosaccharides, and proteins. One difference between isoflavones and the major contaminants is isoflavones contain phenolic moieties, whereas saponins and oligosaccharides do not. While proteins may contain phenolic moieties, the solubility and partitioning of proteins is not typically dominated by these phenolic groups. Oligosaccharides and saponins typically remain soluble in polar solvents regardless of pH and proteins are denatured by organic solvents. Interestingly, the phenolic moiety within isoflavones allows them to be soluble in polar or non-polar (aqueous or organic) solvents depending upon the pH of the solvent.

The present invention recognizes that after having obtained an aqueous plant extract as described above, isoflavones may be isolated by using the following methods.

Scheme I

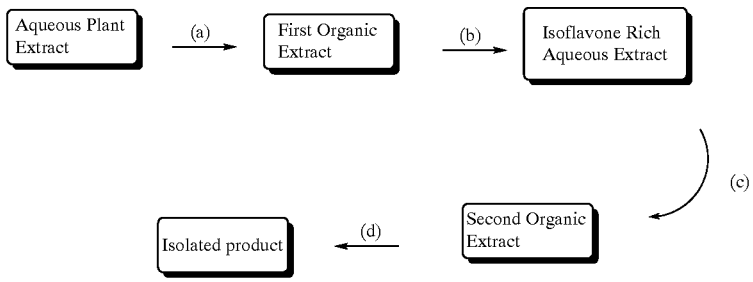

Aqueous plant extracts, as described above, may be employed directly as starting materials for process of the present invention. Alternatively, aqueous plant extracts may be exposed to additional pre-purification steps before processing according to the present invention. Additional pre-purification procedures are well known and include but are Initially, an aqueous alcohol extract is treated to reduce the amount of alcohol present. This reduction aids the efficiency of the subsequent extraction. The reduction in alcohol can be performed by methods well know in the art including azeotropic distillation at ambient or reduced pressure often including the addition of water.

In step (a), the pH of the aqueous plant extract may be adjusted to an approximately neutral pH ranging from about 6 to 8 and extracted with an immiscible organic solvent to yield a first crude organic extract. The extraction can be preformed by methods well known in the art and often comprises numerous washes which are combined to yield the extract. Useful organic solvents include 1-butanol, 2-butanol, t-butanol, pentanol, hexanol, heptanol, octanol, ethyl acetate, tetrahydrofuran, hexane, heptane, octane, isohexane, diethylether, methyl ethyl ketone, diisopropylether, or other ethers, or other polar or non-polar organic solvents which are immiscible with water or mixtures of such solvents. At this stage the isoflavones will be primarily in the organic extract while some proteins, oligosaccharides, and saponins will remain in the aqueous phase.

Alternatively, prior to the first organic extraction the aqueous plant extract can be pretreated at elevated, or lowered, pH to facilitate the subsequent extraction. Many of the components contained in plant extracts are subject to modification by exposure to acidic or basic conditions. These modifications can alter the solubility of the various compounds and make them easier or harder to separate depending on the product sought. For the extraction of isoflavone glycosides, it is preferable to pre-treat the aqueous plant extract at an elevated pH prior to the first extraction step. Treatment at pH between 10 and 12, 11 and 12, or to a particular pH such as 11.1, 11.2, 11.3, 11.4, or 11.5, or any value there between promotes the conversion of both acetyl and malonyl isoflavone derivatives to the glycosolated structure 2 wherein $R_3$ is hydrogen. A skilled artisan would appreciate that the rate of any of these modifications can be increased by raising the temperature. If the temperature is raised too high, however, undesired side reactions or by products may result. Therefore, under certain circumstances, a lower temperature longer reaction may be preferable. Preferably, the temperature of the pH adjusted extract is raised to a temperature above 40° C. The temperature can be raised to between 42° C. and 65° C., 55° C. and 65° C., 57° C. and 62, or to a particular temperature such as 60° C. or any value in between. Preferably the extract is adjusted to a pH of 11.3, heated to 45° C., maintained for 30 minutes, and cooled to approximately room temperature, and the pH adjusted to nearly neutrality, for the next extraction step.

In step (b), the first organic extract is then itself extracted with an aqueous solution having a pH >10, preferably above 11 to yield an isoflavone rich aqueous extract. The specific pH of the extraction is not crucial and is determined by the pKa of the compound being extracted. In the case of isoflavones, a pH of approximately 10–12 is preferred to drive the equilibrium to an extent that most of the phenolic groups are deprotonated and the resulting salts are now water soluble. A pH of 11.2–11.5 is especially preferred. The skilled artisan will appreciate that too high of a pH can have the same detrimental effect as extreme temperature. Often numerous washes are performed and combined to yield the isoflavone rich aqueous extract. If desired the isoflavone rich aqueous extract can be washed with organic solvent for further purity.

In step (c), the pH of the isoflavone rich aqueous extract is then adjusted to approximately neutral (6–8) and extracted with organic solvent to yield a isoflavone rich (second) organic extract. Once again numerous washes are often performed and combined to yield this extract.

Finally, in step (d), the isoflavones are isolated from the isoflavone rich organic extract by standard methods such as drying, chromatography, crystallization or other well known methods. Most conveniently the extract is spray dried to yield the isoflavones of the present invention.

A skilled artisan would appreciate that throughout the Applicant's process it may be advantageous to agitate the various extraction steps or elevate the extraction temperature to achieve more efficient extraction. Such modifications are well known in the art and will be more or less applicable depending on the circumstances. Preferred temperatures are those near ambient (i.e. 15–40 degrees C.) Extraction at reduced temperature may be advantageous if the extract is more stable at such temperature.

Multiple rounds of partitioning, extracting and or purifying can be achieved by performing multiple partitioning steps using polar phases of differing pH. For example, partitioning steps can be alternated between neutral pH and pH above 10.

Alternatively, the aqueous plant extract may be treated as described in Scheme II.

Scheme II

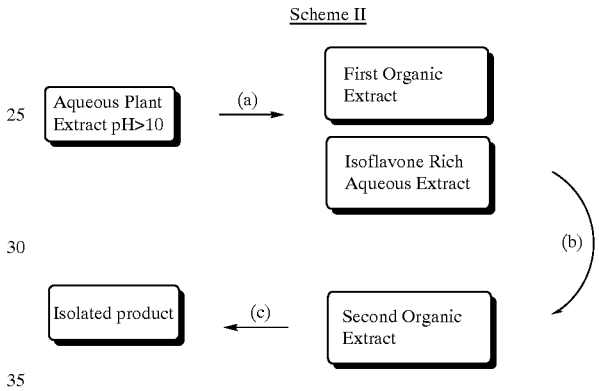

The pH of the starting aqueous plant extract is elevated to greater than 10 and washed with an organic solvent as in step (a) from Scheme I to yield a First Organic Extract and an Isoflavone Rich Aqueous Extract. The resulting First Organic Extract contains impurities and is discarded. The Isoflavone Rich Aqueous Extract is then adjusted to an approximately neutral pH of 6–8 and extracted with an organic solvent as in step (c) from Scheme I to yield a Second Organic Extract. The Second Organic Extract is processed to yield Isolated Product as described in Scheme I above. Preferred isoflavone products of the present invention will have a purity, based on percent by weight of all isoflavones, of between 15 and 70 percent. Preferably the purity will be between about 35% to about 65% and most preferably from about 40% to 50%.

EXAMPLES AND PREPARATIONS

Materials used in these examples may be obtained from well known commercial sources. Reported purity is based on weight percent and yield is based on theoretical amount of starting material present in the processes. Analysis of isoflavone levels was performed by well known methods in the art. (see e.g.; Song, Tongtong; Barua, Kobita; Buseman, Gwen; Murphy, P A, *Soy Isoflavone Analysis: Quality Control and a New Internal Standard.* Am J Clin Nutr 1998;68 (suppl), pp. 1474S–9S; Murphy, P A; Song, T T; Buseman, Gwen; Barua, Kobita; *Isoflavones in Soy-based Infant Formulas.* J. Agric. Food Chem. 1997, 45, 4635–4638; and Wang, H; Murphy, P A; *Isoflavone Content in Commercial Soybean Foods.* J. Agric. Food Chem. 1994, 42, 1666–1673.

Preparation 1

Preparation of a Aqueous Plant Extract from Soy Germ Flour

Hexane Extraction: A product containing greater than 80% soy germ was ground to yield soy flour (soy germ products are well known in the art see U.S. Pat. No. 5,952,230 and WO 96/10341). Soy germ flour 20 kg was extracted with 53.5 kg of boiling hexane for 5 hours with continuous agitation. The extraction slurry was basket-centrifuged at 50° C. to separate the solids from re-claimed hexane to yield a total of 18.6 kg of defatted soybean meal. This defatted soybean meal was air desolventized at room temperature (21–22° C.) for 24 h.

Ethanol extraction and concentration: The desolventized meal was extracted with 290 kg of ethanol/water (80/20, v/v) at 59–62° C. for 15 hours with continuous agitation. The solids were once again isolated by centrifugation. Centrifugation was carried out at 50° C. to yield approximately 17.4 kg of solids and approximately 350 L of crude aqueous extract. The crude extract was then vacuum concentrated at 65–70° C. for about 1 h to a volume of approximately 170 L. The vacuum concentration was continued at 65–70° C. for another 4 h, during which a total of 270 L of soft water was gradually added in order to reduce the ethanol level in the extract. No precipitation or color changes were found during the concentration. A final aqueous extract (weighing 48 kg) was obtained with a residual ethanol level of 825 ppm. The extract was approximately 5.5% solids and 0.3–0.35% isoflavones, 0.3–0.5% saponins, 0.2–0.35% oligosaccharides, and 0.38% protein.

Preparation 2

Preparation of a Aqueous Plant Extract from Commercial Soymeal

Commercial low fiber defatted soymeal (250 g) obtained as white flakes was extracted with 80% ethanol/water (2.5l) for 7 hours at 60° C. The ethanol was evaporated under reduced pressure to yield an aqueous extract (2.0l) that was 17% solids and 0.2% isoflavones.

Preparation 3

Preparation of a Aqueous Plant Extract from Soy Germ

Soygerm obtained at approximately 74% purity was used to make an aqueous extract. Soygerm was ground and defatted with hexane and dried. It was then extracted for 7 hours at 60° C. with 80% ethanol/water. The ethanol was evaporated under reduced pressure to yield an aqueous extract that was 14% solids and 0.86% isoflavones.

Isolation of Isoflavone from Aqueous Plant Extracts

Example 1

The aqueous plant extract from Preparation 1 (100 mL) was adjusted to pH 11.2 using 6 N NaOH. The aqueous phase was then extracted with 1-butanol (100 mL) and the layers separated. The pH of the aqueous phase was adjusted to 6.8 using concentrated HCl and was re-extracted with 1-butanol (60 mL) to yield a second extract. The first extract upon concentration under reduced pressure yielded 1.28 g of yellow solid (3.37% isoflavones), and the second extract upon likewise treatment yielded 0.55 g of pale yellow solid (purity 37.78%, recovery: 56.9%).

Example 2

A sample of the aqueous of plant extract of Preparation 1 was passed through a regenerated cellulose membrane (10,000 MWCO) to obtain 200 mL of a permeate containing isoflavones. The permeate was adjusted to pH 11.2 using 6 N NaOH, extracted at room temperature with 200 ml of butanol, and the layers separated to yield a first extract. The pH of the aqueous phase was adjusted to 6.8 using concentrated HCl and the aqueous phase was extracted with 1-butanol (200 mL) to yield a second extract. The first extract upon concentration under reduced pressure yielded 0.84 g of yellow solid (isoflavone purity 10.48%), and the second extract upon likewise treatment yielded 0.52 g of pale yellow solid (purity: 34.88%, recovery: 38%).

Example 3

The aqueous plant extract from Preparation 1 (100 mL) was adjusted to pH 11.8 using 6 N NaOH and extracted with ethyl acetate (100 mL) and the layers separated to yield a first extract. The pH of the aqueous phase was adjusted to 6.7 using concentrated HCl and it was extracted with ethyl acetate (100 mL) to yield a second extract. The first extract upon concentration under reduced pressure yielded 0.4 g of yellow solid (isoflavones purity: 15.71%). The second extract upon likewise treatment yielded 0.19 g of pale yellow solid (purity: 67.46%, recovery: 32%).

Example 4

The aqueous plant extract from Preparation 3 was diluted two fold with water to obtain a dilute solution (200 mL); the pH was adjusted to 11.24 using 6 N NaOH; the aqueous phase was extracted with 1-butanol (200 mL); and the layers separated to yield a first extract. The pH of the aqueous phase was adjusted to 6.5 using concentrated HCl and it was extracted with 1-butanol (200 mL) to yield a second extract. The first extract upon concentration under reduced pressure yielded 1.57 g of yellow solid (purity 4.5%), and the second extract upon likewise treatment yielded 1.44 g of pale yellow solid (purity: 34.9%, recovery: 72%).

Example 5

The aqueous plant extract from Preparation 1 (200 mL) was heated to 42° C. and its pH adjusted to 11.2 using 6 N NaOH. The mixture was stirred for 15 min. After stirring, the pH was adjusted back to 6.5 using conc. HCl and the mixture cooled to room temperature. The mixture was then extracted with 1-butanol (200 mL). The butanol layer was back-extracted with water at pH 11.2 by stirring for 15 min and separating the layers. The combined aqueous phases were then adjusted to pH 6.5 using concentrated HCl and extracted with 1-butanol (200 mL) to yield a second extract. The second extract upon concentration under reduced pressure yielded 0.93 g of pale yellow solid (purity: 45.38%, recovery: 66.4%, 98.6% of isoflavones are free glycosides, ratio of isoflavones as aglycones is 16.1% genestein, 36.8% glycitein, and 47.1% daidzein).

Example 6

The aqueous plant extract from Preparation 1 (200 mL) was heated to 45° C. and its pH adjusted to 11.3 using 6 N NaOH. The mixture was stirred for 10 min. After stirring, the pH was adjusted back to 6.5 using conc. HCl and the mixture cooled to room temperature. The mixture was then extracted with 1-butanol (2×100 mL). The butanol layer was back-extracted with water at pH 11.2 by stirring for 15 min and the layers separated. The pH of the aqueous phase was adjusted to 6.5 using concentrated HCl and was extracted with 1-butanol (2×100 mL) to yield a second extract. The second extract upon concentration under reduced pressure yielded 1.15 g of pale yellow solid (purity: 42.49%, recovery: 78.2%).

Example 7

The aqueous plant extract from Preparation 1 (200 mL) was heated to 40° C., adjusted to pH 11.3 using 6 N NaOH. The mixture was stirred for 10 min. While stirring, the pH was adjusted back to 6.5 using conc. HCl and cooled to room temperature The mixture was then extracted with 1-butanol (2×100 mL) by stirring and the butanol layer was separated by centrifugation. The butanol layer was back extracted with water at pH 11.2 by stirring for 15 min and the organic layers separated. The pH of the aqueous phase was adjusted to 6.9 using concentrated HCl and it was extracted with 1-butanol (2×100 mL) and the layers separated by centrifugation to yield a second extract. The second extract upon concentration under reduced pressure yielded 1.15 g of pale yellow solid (48.08% isoflavones, 83.6% recovery).

Example 8

The aqueous plant extract from Preparation 2 (70 mL) was diluted to 200 mL with deionized water and warmed to 45° C. The pH was adjusted to 11.3 with 6N NaOH, stirred for 15 minutes, allowed to cool to room temperature. The pH was adjusted back to 6.5 with concentrated sulfuric acid and the mixture extracted with 1-butanol (2×100 mL). To the butanol phase was added 200 mL of water and the pH was adjusted to 11.3 with 6N NaOH. The layers were separated and the pH of the aqueous layer was adjusted back to 6.5 with sulfuric acid and then extracted with 1-butanol (2×100 mL). The butanol was evaporated under reduced pressure to yield 0.39 g of a pale yellow solid (24.44% isoflavones, 86.5% recovery).

Example 9

Novasoy® (1 g) was stirred into 75 mL 1-butanol, 50 mL water, and 25 mL brine and the layers separated. The butanol phase was added to 75 mL water and the pH was adjusted to 11.3 with 6N NaOH with stirring. The layers were separated and the aqueous phase was adjusted to pH 6.3 with HCl and extracted with butanol (1×75 mL). The butanol was evaporated under reduced pressure to yield 0.34 g of a tan solid (58.3% isoflavones, 51.7% recovery).

Example 10

The aqueous plant extract from Preparation 1 (100 mL) was heated to 60° C. and adjusted to pH 11.2 using 6 N NaOH. The mixture was stirred for 10 minutes. After stirring, the pH was adjusted back to 6.5 using concentrated HCl and the mixture allowed to cool to room temperature. The mixture was then extracted with 100 ml of solvent (mixture of 1-butanol and ethyl acetate in a 1:1 ratio) by shaking and layers separated Water (100 ml) was added to the organic phase and the mixture stirred while the pH was adjusted to 9.3 with 6 N NaOH. The layers were then separated and the aqueous phase adjusted to pH 6.5. The aqueous layer was then extracted again with a 1:1 mixture of 1-butanol/ethyl acetate, the solvent layer isolated, and evaporated under reduced pressure to yield 0.11 g of an off-white solid (37.25% isoflavones; 13.05% recovery).

Example 11

The aqueous plant extract from Preparation 1 (100 mL) was heated to 60° C. and adjusted to pH 11.2 using 6 N NaOH. The mixture was then extracted with 1-pentanol (100 mL at room temperature). The aqueous phase was removed, cooled to room temperature, adjusted to pH 6.5 with concentrated HCl, and extracted with 1-pentanol (100 mL). The 1-pentanol layer was then evaporated under reduced pressure to yield 0.63 g of a golden yellow solid (27.1% isoflavones, 67% recovery).

Example 12

The aqueous plant extract in Preparation 1 (6000 mL) was adjusted to pH 11.3 for 30 minutes with 6 N NaOH, and was adjusted back to pH 6.5 with concentrated sulfuric acid while stirring. It was concentrated from 6 liters to 1 liter by evaporation and extracted with 1-butanol (2×1000 mL). The insoluble solids at the interface were removed by centrifugation. The combined butanol layers were back extracted with water at pH 11.3 (4×250 mL). The first fraction of aqueous backwash was adjusted to pH 6.5 with concentrated sulfuric acid and cooled to 2 C overnight. 6.99 g of precipitate were collected by vacuum filtration and dried in a vacuum oven at 60 C and 2 mm Hg. (82.1% isoflavones, 60% recovery)

Example 13

The aqueous plant extract in Preparation 1 (1000 mL) was adjusted to pH 11.3 with 6 N NaOH with stirring for 45 minutes and readjusted to pH 6.5 with concentrated sulfuric acid. The solution was concentrated to dryness by rotary evaporation and dried in a vacuum oven to produce 69 g of solids. 12.39 g of these solids was added to a beaker with 200 mL of 1-butanol saturated with water and stirred vigorously for 1 hour. The butanol was decanted off and 200 mL of water was added to the butanol. The pH of the solution was adjusted to 11.3 with 6 N NaOH. The layers were separated and 100 mL of the aqueous phase was adjusted to pH 6.5 with concentrated sulfuric acid. The aqueous solution was extracted with 1-butanol (1×100 mL). The final butanol phase was dried by rotary evaporation to produce 0.5 g of an off-white powder having complete solubility at 0.03% wt/vol. (37.66% isoflavones, 57.6% recovery)

Example 14

The aqueous plant extract from Preparation 1 (10000 mL) was adjusted to pH 11.3 and maintained for 90 minutes at room temperature with stirring. The pH was adjusted back to about 6.5 using concentrated sulfuric acid. The mixture was then extracted with 1-butanol (3×2500 mL) at room temperature. The emulsion phase was centrifuged during the third stage to further separate the solvent from the aqueous phase. The three butanol solutions were combined and 5000 mL of water was added. The pH of the combined solution was adjusted to 11.4 with 6 N NaOH while stirring. The layers were separated and the emulsion phase was again centrifuged. The pH of the aqueous phase was adjusted to 6.5 with concentrated sulfuric acid while stirring. This aqueous phase was extracted again with 1-butanol (2×2500 mL) at room temperature. The butanol phases were combined and the solvent evaporated by rotary evaporation to yield 45.41 g of off-white solid (49.51% isoflavones, 70.4% recovery).

Example 15

Isolation of Flavanones

Flavanones were isolated from Kinnow Extract (Mandarin from USDA) according to the following procedure. The aqueous extract used as a starting material was extracted with 1-butanol (1×) by stirring and the butanol layer was separated to yield an intermediate extract. The butanol layer was back extracted with water at pH 11.2 by stirring for 15 min and the organic layers separated. The pH of the aqueous phase was adjusted to 6.5 using concentrated HCl and it was extracted with 1-butanol (1×) and the layers separated by centrifugation to yield a second extract. The intermediate and second extract was assayed for Hesperidin and Didymin according to known procedures. (see e.g. Merken supra).

| Flavanone | Starting Aqueous Extract | Inter. Extract | 2nd Extract |
|---|---|---|---|
| Hesperidin | 10896 µg/g | 16624 µg/g | 73284 µg/g |
| Didymin | 3137 µg/g | 8575 µg/g | 30304 µg/g |

Example 16

Isolation of Flavonols

Flavonols were isolated from Gunpowder Tea-Pin Head Variety according to the following procedure. The aqueous extract was used as a starting material and was extracted with 1-butanol (1×) by stirring and the butanol layer was separated by centrifugation to yield an intermediate extract. The butanol layer was back extracted with water at pH 11.3 by stirring for 15 min and the organic layers separated. The pH of the aqueous phase was adjusted to 6.4 using concentrated HCl and it was extracted with 1-butanol (1×) and the layers separated by centrifugation to yield a second extract. The intermediate and second extract was assayed for the listed flavonols according to known procedures. (see e.g. Merken supra).

| Flavonol | Starting Aqueous Extract | Inter. Extract | 2nd Extract |
|---|---|---|---|
| Quercetin-3-rutinoside | 98 µg/g | 1328 µg/g | 2356 µg/g |
| Quercetin-3-D galactoside | 103 µg/g | 1374 µg/g | 1940 µg/g |
| Quercetin-3-rhamnoside | 202 µg/g | 2894 µg/g | 6755 µg/g |

Example 17

Isolation of Flavonols

Flavonols were isolated from Buckwheat Farinetta® according to the following procedure. The aqueous extract was used as a starting material and was extracted with 1-butanol (1×) by stirring and the butanol layer was separated by centrifugation to yield an intermediate extract. The butanol layer was back extracted with water at pH 11.2 by stirring for 15 min and the organic layers separated. The pH of the aqueous phase was adjusted to 6.4 using concentrated HCl and it was extracted with 1-butanol (1×) and the layers separated by centrifugation to yield a second extract. The intermediate and second extract was assayed for the listed flavanols according to known procedures. (see e.g. Merken supra).

| Flavonol | Inter. Extract | 2nd Extract |
|---|---|---|
| Quercetin-3-rutinoside | 563 µg/g | 1290 µg/g |
| Quercetin-3-rhamnoside | 109 µg/g | 602 µg/g |

Comparative Assessments of High Concentrate Isoflavone Products

A. Color Determination

Color of the various isoflavone products was determined using following procedure on a the ColorQuest XE by HunterLab (Reston, Va.). This instrument is a dual beam, xenon flash spectrophotometer. The color is characterized by three distinct values, the L-value, a-value and b-value. The L-value corresponds to brightness, with a higher value corresponding to a brighter product. The a-value assesses the red/green coloration with positive and negative values corresponding to the degree of red and green, respectively. Similarly, the b-value quantifies the degree of yellow/blue coloration with positive values relating to yellow hues and negative values to blue.

1. Standardize the spectrophotometer using the following settings:
    a. Set mode type to "Reflectance, Specular Exclusion (RSEX)"
    b. Set area view to "Small"
    c. Set port size to "0.375 inches"
    d. Follow software standardization procedures using white tile for calibration
2. For each product, place sample in the 20-mm transmission cell to completely cover the reflectance port. Fill to slightly more than half the height of the cell.
3. Tap the base of the cell to remove any visible clumps of product and ensure homogeneity.
4. Place the transmission cell with sample in front of the reflectance port, cover with the light trap and run instrument to characterize sample color.

B. Water Solubility

Water solubility was determined using the following procedure.

1. Weigh 50.0 g of deionized water at 20° C. into a 100-mL beaker.

2. Weigh about 0.05 g of the sample, then add to the water using a stir bar for mixing. Make sure to record the exact mass of the added sample.
3. If the sample readily disperses, add another 0.05 g and adequately mix. Continue the process until the solubility limit has been exceeded, making sure to record the weight of each additional amount of sample.
4. Allow the mixture to stir for 30 minutes.
5. Weigh and record the mass of a Whatman #4 filter paper.
6. Using a Buchner funnel under a vacuum, filter the solution through the pre-weighed paper to remove any insoluble material.
7. Weigh an aluminum pan, then place the filter paper with residue in the pan.
8. Dry the samples in a vacuum desiccator for 48 hours at room temperature.
9. Weigh the pan, filter paper and insoluble material following drying. Calculate the weight of water-soluble material and percent solubility.

Results:

The color, solubility, and other characteristics of the products of the present invention were compared to commercially available isoflavone products from NovaSoy®, Solbar, and Central Soya. Results are summarized in Tables 3–6 below.

TABLE 3

Color of Commercially Available High Isoflavone (40%) Products

| Isoflavone Products | Color | | |
|---|---|---|---|
| | L-value | a-value | b-value |
| Solbar | 51.72 | 7.91 | 29.82 |
| NovaSoy ® | 58.48 | 7.41 | 28.33 |
| Central Soya | 58.95 | 5.22 | 21.14 |
| Example #5 | 78.34 | 1.09 | 18.79 |

Visually, the products of the present invention have a light tan to cream coloration compared to the redder appearance of the other commercially available products. This observation was confirmed by the color results from the Hunter spectrophotometer. The products of the present invention are significantly brighter, as indicated by its higher L-value. They also have less red coloration (lower a-value) than the examined commercial high isoflavone products. Also, both the Solbar and Novasoy® products have a stronger yellow hue than then products of the present invention. Isoflavone compositions of the present invention will preferably have L-values greater than about 65 and more preferably greater than about 75, or between about 65 and 75. Isoflavone compositions of the present invention will preferably have a-values lower than about 4 and more preferably lower than about 2, or between 2 and 4.

TABLE 4

Solubility of Commercially Available High Isoflavone (40%) Products 0.03% in water

| 40% Isoflavone Products | Percent Soluble | Percent Insoluble |
|---|---|---|
| Solbar | 61.50% | 38.50% |
| Novasoy | 75.93% | 24.07% |

TABLE 4-continued

Solubility of Commercially Available High Isoflavone (40%) Products 0.03% in water

| 40% Isoflavone Products | Percent Soluble | Percent Insoluble |
|---|---|---|
| Central Soya | 45.56% | 54.44% |
| Example 13 | 100.00% | — |

The Central Soya product resulted in a golden to light brown precipitate, while the other two products had a white precipitate. Following the solubility assessment, the supernatant was removed to determine the effect of each product on the color of the liquid. The Novasoy® product had a significantly greater yellow appearance, as indicated by its high b-value, as well as a slight green tinge. Solbar product resulted in a similar color tendency, but not quite as strong as Novasoy®. Although the Central Soya and product of the present invention had faint bluish hues, shown by the negative b-values from the Hunter readings, this coloration was barely noticeable compared to the control water sample.

TABLE 5

Room Temperature Stability and Color of High Isoflavone Products in 0.03% (w/w) Solutions in Water

| Isoflavone Products | Precipitate | Color | | |
|---|---|---|---|---|
| | | L-value | a-value | b-value |
| Deionized Water | — | 1.50 | −0.18 | −0.26 |
| Solbar | Y (white ppt.) | 7.70 | −1.43 | 1.32 |
| Novasoy ® | Y (white ppt.) | 4.23 | −1.73 | 4.10 |
| Central Soya | Y (golden ppt.) | 5.78 | −0.88 | −0.92 |
| Example #5 | N | 3.20 | −0.58 | −1.09 |

Material from Example 13 was readily dispersible in water, completely soluble, and resulted in a clear and virtually colorless solution. Compared to commercially available products, the products of the present invention demonstrate significant advantages. These advantages would be especially important in beverage applications.

The isoflavone products of the present invention can exist almost exclusively in the free glycosidic form (i.e. structure 2 wherein $R_3$ is hydrogen). In preferred embodiments, greater than 95% of the isoflavones exist as free glycosides, more preferably greater than 98% exist as free glycosides. In addition, the isoflavones isolated from soy germ have a lower level of genistin than isoflavones from different sources. Being able to vary the profile of isoflavones can have a desirable effect on their potency. Accordingly, preferred embodiment of the present invention are those wherein: the composition comprises daidzin and genistin and the ratio of the weight percent of daidzin to the weight percent of genistin is greater than one, and more preferably greater than 2. Another preferred composition is one wherein the composition comprises glycitin and genistin and the ratio of the weight percent of glycitin to the weight percent of genistin is greater than one and more preferably is greater than 2.

TABLE 6

Isoflavone profile data and other analytical results.

| Analytical Method | | Example 14 | Novasoy ® | Solbar | Central Soya | Example 14 Rerun |
|---|---|---|---|---|---|---|
| | Isoflavones (%) | 46.95 | 38.31 | 40.79 | 38.9 | 49.51 |
| | Isoflavones (ppm) | 469547 | 383092 | 407877 | 389012 | 495111 |
| | Daidzin (ppm) | 207814 | 149971 | 102276 | 109065 | 245808 |
| | Genistin (ppm) | 67848 | 181075 | 278743 | 263786 | 73300 |
| | Glycitin (ppm) | 144543 | 28245 | 15975 | 5956 | 165517 |
| | Daidzein (ppm) | 28807 | 3111 | 5715 | 5319 | 5729 |
| | Genistein (ppm) | 3953 | 2228 | 3681 | 3226 | 994 |
| | Glycitein (ppm) | 16010 | 2202 | 1487 | 489 | 3763 |
| | Acetyl Daidzin (ppm) | 406 | 7677 | | 516 | |
| | Acetyl Genistin (ppm) | 166 | 7171 | | 655 | |
| | Acetyl Glycitin (ppm) | | | 1412 | | |
| AOAC 968.06 | Protein (%) | 2.73 | 9.13 | 4.48 | 15.94 | |
| AOAC 922.06 | Fat (%) | 16.9 | 5.72 | 14.7 | 4.54 | |
| AOAC 923.03 | Ash (%) | 2.12 | 33.06 | 33.72 | 38.17 | |
| AOAC 926.08 | Moisture (%) | 4.88 | 2.8 | 5.64 | 3.76 | |

A number of embodiments of the invention have been described. Nevertheless, it will be understood that various modifications may be made without departing from the spirit and scope of the invention. For example, there is a wide variety of plant materials from which the isoflavone-containing extract can be derived. Accordingly, other embodiments are within the scope of the following claims.

We claim:

1. A method for isolating phenolic compounds comprising the steps of:
   (a) providing an aqueous plant extract at a first pH greater than 10, the aqueous plant extract comprising phenolic compounds, wherein the aqueous plant extract is obtained from a plant selected from the group consisting of soybean, chick pea, red clover, subterranean clover, ground pea, milk vetch, marama bean, sword bean, jack bean, seaside sword bean, carao bean, cluster bean, balu, hyacinth bean, grass pea, Indian vetch, garden pea, djenko bean, goa bean, yam bean, broad bean, earth pea, lentil, jumping bean, alfalfa, velvet bean, African locust bean, inga, Cyprus vetch, yebnut, tallow tree, Polynesian chestnut, kudzu root, oil bean tree, mesquite, tamarind, fenugreek, Indian licorice, ground nut, kinnow, gunpowder tea, buckwheat, clover, and preparations thereof;
   (b) washing the aqueous plant extract with an organic solvent wherein the organic solvent is selected from 1-butanol, 2-butanol, t-butanol, pentanol, hexanol, heptanol, octanol, ethyl acetate, tetrahydrofuran, hexane, heptane, octane, isohexane, diethylether, methyl ethyl ketone, diisopropylether, or a polar or non-polar organic solvent which is immiscible with water or mixtures thereof, to yield an aqueous phase and an organic phase;
   (c) adjusting the pH of the aqueous phase to a pH of less than 9 to yield a pH-adjusted aqueous phase; and
   (d) isolating flavonoid, anthocyanidin, flavone, flavonol, flavanone, isoflavone, glycosylated isoflavone, or proanthocyanidin compounds from the pH-adjusted aqueous phase.

2. The method of claim 1 wherein the aqueous plant extract is from a soybean.

3. The method of claim 2 wherein the aqueous plant extract is from de-fatted soygerm.

4. The method of claim 1 wherein step (c) comprises adjusting the pH of the aqueous phase to a pH from about 6 to about 8.

5. The method of claim 1 wherein the organic solvent is immiscible with water.

6. The method of claim 1 wherein the organic solvent is selected from the group consisting of 1-butanol, 2-butanone, ethylacetate, and isopropyl alcohol.

7. The method of claim 1 wherein step (a) comprises:
   providing an initial aqueous plant extract;
   extracting with an organic solvent to yield an organic solution and
   extracting with an aqueous solution having a pH greater than 10 to yield an aqueous plant extract.

8. The method of claim 1 wherein step (a) comprises:
   providing an aqueous alcohol plant extract;
   reducing the amount of alcohol present in the aqueous alcohol plant extract;
   extracting with an organic solvent to yield an organic solution and
   extracting with an aqueous solution having a pH greater than 10 to yield an aqueous plant extract.

9. The method of claim 1 wherein step (a) comprises:
   providing an initial aqueous plant extract;
   adjusting the pH of the aqueous plant extract to a pH greater than about 10;
   extracting with an organic solvent to yield an organic solution and
   extracting with an aqueous solution having a pH greater than 10 to yield an aqueous plant extract.

10. The method of claim 1 wherein step (d) comprises:
    extracting the pH-adjusted aqueous phase with an organic solvent to form a final organic phase and a final aqueous phase; and
    isolating phenolic compounds from the final organic phase.

11. The method of claim 1 wherein step (d) comprises drying.

12. The method of claim 11 wherein step (d) comprises spray drying.

13. The method of claim 1, wherein step (d) comprises chromatography.

14. The method of claim 1, wherein step (d) comprises crystallization.

15. The method of claim 1, wherein isolating phenolic compounds comprises isolating desired phenolic compounds.

16. A method, comprising:
providing an aqueous soybean extract at a pH greater than 10, wherein the aqueous soybean extract comprises a plurality of phenolic compounds;
washing the aqueous soybean extract with an organic solvent wherein the organic solvent is selected from 1-butanol, 2-butanol, t-butanol, pentanol, hexanol, heptanol, octanol, ethyl acetate, tetrahydrofuran, hexane, heptane, octane, isohexane, diethylether, methyl ethyl ketone, diisopropylether, or a polar or non-polar organic solvent which is immiscible with water or mixtures thereof, to yield an aqueous phase and an organic phase;
adjusting the pH of the aqueous phase to a pH of less than 9 to yield a pH-adjusted aqueous phase; and
isolating flavonoid, anthocyanidin, flavone, flavonol, flavanone, isoflavone, glycosylated isoflavone, or proanthocyanidin compounds from the pH-adjusted aqueous phase.

17. The method of claim 16, wherein the aqueous soybean extract is from de-fatted soygerm.

18. The method of claim 16, wherein adjusting the pH comprises adjusting the pH of the aqueous soybean extract to a pH from about 6 to about 8.

19. The method of claim 16, wherein the organic solvent is immiscible with water.

20. The method of claim 16, wherein the organic solvent is selected from the group consisting of 1-butanol, 2-butanone, ethylacetate, and isopropyl alcohol.

21. The method of claim 16, wherein providing an aqueous soybean extract comprises:
providing a preliminary aqueous soybean extract;
extracting with an organic solvent to yield an organic solution; and
extracting the organic solution with an aqueous solution having a pH greater than 10 to yield an aqueous soybean extract.

22. The method of claim 16, wherein providing an aqueous soybean extract comprises:
providing an aqueous alcohol soybean extract;
reducing the amount of alcohol present in the aqueous alcohol soybean extract;
extracting with an organic solvent to yield an organic solution; and
extracting the organic solution with an aqueous solution having a pH greater than 10 to yield an aqueous soybean extract.

23. The method of claim 16, wherein providing an aqueous soybean extract comprises:
providing a preliminary aqueous soybean extract;
adjusting the pH of the preliminary aqueous soybean extract to a pH greater than about 10;
extracting with an organic solvent to yield an organic solution; and
extracting the organic solution with an aqueous solution having a pH greater than 10 to yield an aqueous soybean extract.

24. The method of claim 16, wherein isolating flavonoid, anthocyanidin, flavone, flavonol, flavanone, isoflavone, glycosylated isoflavone, or proanthocyanidin compounds from the pH-adjusted aqueous phase comprises extracting the pH-adjusted aqueous phase with an organic solvent to form a final organic phase and a final aqueous phase.

25. The method of claim 24, further comprising isolating flavonoid, anthocyanidin, flavone, flavonol, flavanone, isoflavone, glycosylated isoflavone, or proanthocyanidin compounds from the final organic phase.

26. The method of claim 16, wherein isolating comprises drying.

27. The method of claim 16, wherein isolating comprises spray drying.

28. The method of claim 16, wherein isolating comprises chromatography.

29. The method of claim 16, wherein isolating comprises crystallization.

\* \* \* \* \*